United States Patent [19]

Siuta et al.

[11] 4,229,372

[45] Oct. 21, 1980

[54] UREYLENE PHENYLENE ANIONIC NAPHTHALENESULFONIC ACIDS

[75] Inventors: Gerald J. Siuta, Yonkers; Ransom B. Conrow, Pearl River; John F. Poletto, Nanuet; Seymour Bernstein, New City, all of N.Y.

[73] Assignee: American Cyanamid Company, Stamford, Conn.

[21] Appl. No.: 17,206

[22] Filed: Mar. 5, 1979

Related U.S. Application Data

[62] Division of Ser. No. 923,746, Jul. 11, 1978, Pat. No. 4,155,931.

[51] Int. Cl.$^2$ ............................................. C07C 143/30
[52] U.S. Cl. ................................................. 260/507 R
[58] Field of Search ..................................... 260/507 R

[56] References Cited

U.S. PATENT DOCUMENTS

| 2,164,229 | 6/1939 | Coulthand | 260/507 R |
| 3,312,707 | 4/1967 | Jones | 260/507 R |

*Primary Examiner*—Paul J. Killos
*Attorney, Agent, or Firm*—Claude J. Caroli

[57] ABSTRACT

Novel ureylenebis-[substituted-phenylenecarbonylimino-substituted-phenylenesulfonylimino]naphthalenetrisulfonic acid alkali metal salts], useful as inhibitors of the complement system of warm-blooded animals, the amino-substituted phenylenecarbonyl imino, substituted-phenylenesulfonylimino-naphthalenetrisulfonic acid, alkali metal salts, which are new intermediates for the preparation of the active ureylenes, and the process for their preparation.

8 Claims, No Drawings

UREYLENE PHENYLENE ANIONIC NAPHTHALENESULFONIC ACIDS

This is a division of application Ser. No. 923,746 filed July 11, 1978 now U.S. Pat. No. 4,155,931.

BACKGROUND OF THE INVENTION

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in the body processes can be found in, for example, Bull. World Health Org., 39, 935–938 (1968); Ann. Rev. Medicine, 19, 1–24 (1968); The John Hopkins Med. J., 128, 57–74 (1971); Harvey Lectures, 66, 75–104 (1972); The New England Journal of Medicine, 287, 452–454; 489–495; 545–549; 592–596; 642–646 (1972); Scientific American, 229, (No. 5), 54–66 (1973); Federation Proceedings, 32, 134–137 (1973); Medical World News, Oct. 11, 1974, pp. 53–66; J. Allergy Clin. Immunol., 53, 298–302 (1974); Cold Spring Harbor Conf. Cell Proliferation 2/Proteases Biol. Control/229–241 (1975); Ann. Review of Biochemistry, 44, 697 (1975); Complement in Clinical Medicine, Disease-a-Month, (1975); Complement, Scope, December 1975; Annals of Internal Medicine, 84, 580–593 (1976); "Complement: Mechanisms and Functions", Prentice-Hall, Englewood Cliffs, N.J. (1976); Essays Med. Biochem., 2, 1–35 (1976); Hospital Practice, 12, 33–43 (1977); Perturbation of Complement in Disease, Chap. 15 in Biological Amplification Systems in Immunology (Ed. Day and Good), Plenum, New York and London (1977); Am. J. Clin. Pathology, 68, 647–659 (1977).

The complement system can be considered to consist of three sub-systems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is non-specific; it destroys invaders only because it is generated in their neighborhood. In order to minimize damage to the host's cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain of the complement proteins, suggestions regarding the mode of complement binding to biological membranes and the manner in which complement effects membrane damage are discussed in Annual Review in Biochemistry, 38, 389 (1969); Journal of Immunology, 119, 1–8, 1195, 1358–1364, 1482 (1977).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)benzenesulfonic acid], tetrasodium salt (chlorazol fast pink); heparin and a sulphated dextran have been reported to have an anticomplementary effect, British Journal of Experimental Pathology, 33, 327–339 (1952). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, Journal of Medicinal Chemistry, 12, 415–419; 902–905; 1049–1052; 1053–1056 (1969); Canadian Journal of Biochemistry, 47, 547–552 (1969); The Journal of Immunology, 104, 279–288 (1970); The Journal of Immunology, 106, 241–245 (1971); The Journal of Immunology, 111, 1061–1066 (1973); Biochim. Biophys. Acta, 317, 539–548 (1973); Life Sciences, 13, 351–362 (1973); Journal of Immunology, 113, 584 (1974); Immunology, 26, 819–829 (1974); Journal of Medicinal Chemistry, 17, 1160–1167 (1974); Biochim. Biophys. Res. Comm., 67, 225–263 (1975); Ann. N.Y. Acad. Sci., 256, 441–450 (1975); Journal of Medicinal Chemistry, 19, 634–639, 1079 (1976); Journal of Immunology, 118, 466 (1977); Arch. Int. Pharmacodyn., 226, 281–285 (1977); Biochem. Pharmacol. 26, 325–329 (1977); Journal Pharm. Sci., 66, 1367–1377 (1977); Chem. Pharm. Bull., 25, 1202–1208 (1977); Biochim.

Biophys. Acta, 484, 417–422 (1977) and Journal Clin. Microbiology, 5, 278–284 (1977).

It has been reported that the known complement inhibitors epsilon-aminocaproic acid and tranexamic acid have been used with success in the treatment of hereditary angioneurotic edema, a disease state resulting from an inherited deficiency or lack of function of the serum inhibitor of the activated first component of complement (C1 inhibitor), The New England Journal of Medicine, 286, 808–812 (1972), 287, 452–454 (1972); Ann. Intern. Med., 84, 580–593 (1976); J. Allergy and Clin. Immunology, 60, 38–40 (1977).

It has also been reported that the drug pentosanpolysulfoester has an anticomplementary activity on human serum, botn in vitro and in vivo, as judged by the reduction in total hemolytic complement activity; Pathologie Biologie, 25, 33–36, 25 (2), 105–108, 25 (3), 179–184 (1977).

It is known that the compound Suramin is moderately active as a complement inhibitor, and possesses the structure:

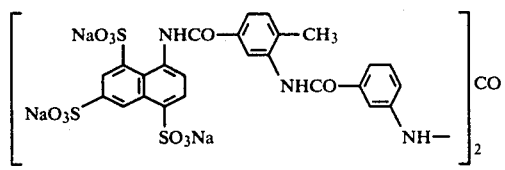

It now has been discovered that certain modifications of this structure provide compounds with enhanced inhibitory activity. This invention is based on such modifications.

The following publications, pertaining to the chemistry of Suramin, are related to the preparation of the novel compounds of this invention:

Bayer & Co., D.R.P. 278,122, June 22, 1913 [C.A. 9, 1096 (1915)]
Bayer & Co., D.R.P. 288,272, Jan. 23, 1914 [C.A. 10, 2279 (1916)]
Bayer & Co., D.R.P. 288,273, Feb. 21, 1914 [C.A. 10, 2279 (1916)]
Frdl. 12, 185–186, 191–195 (1914–1916)
Danish Pat. No. 20,743 (1915)
Austrian Pat. No. 72,298 (1916)
Austrian Pat. No. 72,303 (1916)
U.S. Pat. No. 1,218,654 (1917)
U.S. Pat. No. 1,218,655 (1917)
Austrian Pat. No. 73,381 (1917)
U.S. Pat. No. 1,308,071 (1919)
E. Fourneau, J. Tréfouel, Mme. J. Tréfouel and J. Vallee, Acad. Sci. Comp. Rend., 178, 675–676 (1924)
E. Fourneau, F. Tréfouel and J. Vallee, Ann. de L'Institut Pasteur, 38 (2), 81–114 (1924)
B. Heymann, Zeitschrift Ang. Chem., 37, 585–589 (1924)
British Pat. No. 224,849 (1925)
U.S. Pat. No. 1,606,624 (1926)
J. E. R. McDonagh, Brit. Med. J., 693–696 (1926) [Chem. Zentralblatt, 1769–1770 (1926 II)]
W. Roehl, Arch. Schiff. Trop. Hyg., 30 (1), 103–111 (1926)
Poulenc Fréres, D.R.P. 427,857, April 20, 1926 [Frdl. 15, 1434–1436 (1928)]
I. E. Balaban and H. King, J. Chem. Soc., 3068–3097 (1927)
H. Bauer and J. Becker, Arb. Staatsinst. Exptl. Therap., 16 pp. (1928)
U.S. Pat. No. 1,968,820 (1934)
O. Yu. Magidson, O. S. Madaeva and M. V. Rubtzov, Khim. Farm. Prom., 2, 89–94 (1935) [C.A., 30, 4492 (1936)]
U.S. Pat. No. 2,126,180 (1938)
P. Pratsi and L. Raffa, Farmaco Sci e Tec (Pavia), 1, 21–34 (1946)
A. Spinks, Biochem. J., 42, 109–116 (1948)
E. D. Wills and A. Wormall, Biochem., J., 47, 158–170 (1950)
German Pat. No. 890,952 (1953) [C.A. 52, 14693 (1958)]
A. Adams, J. N. Ashley and H. Bader, J. Chem. Soc., 3739–3744 (1956) [C.A. 51, 4375i]

Publications related to the biological use of Sumarin compounds for the purpose of inhibiting the compelement system, including humans, as determined by the in vivo and in vitro testing of the blood serum of warm-blooded animals are:

B. Stuber and K. Lang, Arch. Exptl. Path. Pharmacol., 154, 41–49 (1930) [C.A. 25, 3067 (1931)]
F. Klopstock, Zeitschrift für Immunitatsforschung und experimentalle Therapie, 75, 348–354 (1932)
H. J. Schmid, Schweiz. Med. Woch., 96, 1267–1269 (1966)
K. Lauenstein, Bayer-Symposium I, 25–30 (1969)
J. S. C. Fong and R. A. Good, Clin. Exp. Immunol., 10, 127–138 (1972)
V. Eisen and C. Loveday, Br. J. Pharmac., 49, 678–687 (1973)
D. Brackertz and F. Kueppers, Allergol. Et. Immunopath., 11, 163–168 (1974)
E. Raepple, H-U. Hill and M. Loos, Immunochemistry, 13 (3), 251–255 (1976).

SUMMARY OF THE INVENTION

This invention is concerned with ureylenebis[sub-stituted-phenylenecarbonylimino-substituted-phenylenesulfonylimino]naphthalenetrisulfonic acids and all pharmaceutically acceptable salts thereof, having complement inhibiting activity, which are new compounds of the general formulae:

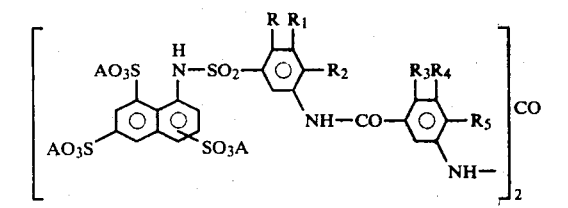

and

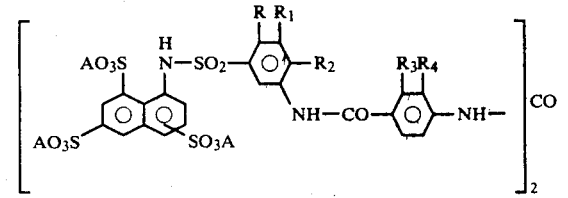

wherein R and $R_2$ are selected from the group consisting of hydrogen and methyl; $R_1$ and $R_4$ are selected from the group consisting of hydrogen and —COOB, wherein B is selected from the group consisting of hydrogen and a pharmaceutically acceptable salt cation; $R_3$ is selected from the group consisting of hydrogen and —SO$_3$A, wherein A is a pharmaceutically acceptable salt cation; R$_5$ is selected from the group consisting of hydrogen and methyl; with the proviso that R$_1$, R$_3$ and R$_4$ may not all be hydrogen; with the second proviso that R$_2$ and R$_5$ may not both be hydrogen; with the third proviso that neither phenyl moiety can contain both —SO$_3$A and —COOB.

A preferred embodiment of this invention consists of those compounds wherein either R$_1$ or R$_4$, or both, are —COOB; and R$_3$ is hydrogen.

Another preferred embodiment of this invention consists of those compounds wherein R$_3$ is —SO$_3$A; and R$_1$ and R$_4$ are hydrogen.

This invention is also concerned with compounds of the formulae:

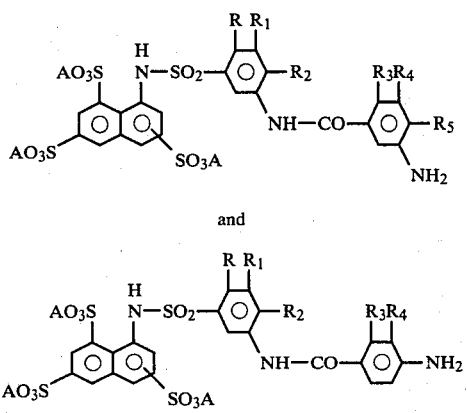

and wherein R and R$_2$ are selected from the group consisting of hydrogen and methyl; R$_1$ and R$_4$ are selected from the group consisting of hydrogen and —COOB, wherein B is selected from the group consisting of hydrogen and a pharmaceutically acceptable salt cation; R$_3$ is selected from the group consisting of hydrogen and —SO$_3$A, wherein A is a pharmaceutically acceptable salt cation; R$_5$ is selected from the group consisting of hydrogen and methyl; with the proviso that R$_1$, R$_3$ and R$_4$ may not all be hydrogen; with the second proviso that R$_2$ and R$_5$ may not both be hydrogen; with the third proviso that neither phenyl moiety can contain both —SO$_3$A and —COOB; said compounds being useful as intermediates for the preparation of the complement inhibiting compounds described above. Some of the intermediate compounds also possess complement inhibiting activity.

DESCRIPTION OF THE INVENTION

The novel intermediate amine compounds of the invention are prepared by reacting the appropriate 8-amino-1,3,5 (and 1,3,6)naphthalenetrisulfonic acid, trialkali metal salt with a nitrobenzenesulfonyl chloride such as 2-methyl-5-nitrobenzenesulfonyl chloride, 4-methyl-3-nitrobenzenesulfonyl chloride and 5-nitro-2,4-xylenesulfonyl chloride, for 1.5-36 hours in an aqueous solution made alkaline with alkali metal hydroxide, anhydrous alkali metal carbonate or alkali metal acetate trihydrate. After neutralization, the solution is diluted with absolute ethanol to provide the corresponding nitro substituted phenylenesulfonylamino-1,3,5 (and 1,3,6)-naphthalenetrisulfonic acid, trialkali metal salt.

Hydrogenation of the preceding nitro trialkali metal salts using 10% palladium-carbon catalysts, filtration, concentration and treatment with absolute ethanol provides the corresponding amino substituted-phenylenesulfonylimino naphthalenetrisulfonic acid, trialkali metal salt compounds.

The amino compounds above, dissolved in aqueous media and made alkaline with either alkali metal hydroxide or anhydrous alkali metal carbonate are reacted with a nitro-sulfobenzoic acid anhydride such as 4-nitro-2-sulfobenzoic acid anhydride or with a nitrobenzoyl chloride such as 3-nitro-p-toluoyl chloride, 5-nitroisophthaloyl chloride and 3-carbomethoxy-5-nitrobenzoyl chloride for 1.5-36 hours. After neutralization, the solution is diluted with absolute ethanol to provide the corresponding nitro substituted-phenylenecarbonylimino, substituted-phenylenesulfonyliminonaphthalenetrisulfonic acid, trialkali metal salt.

The novel intermediate amine compounds of the invention are then obtained by hydrogenation of the above nitro compounds using 10% palladium-carbon catalyst in water as previously described, filtration and evaporation of the filtrate produces a residue which is dissolved in water and precipitated with absolute ethanol to provide the desired product.

The novel ureylene compounds of the invention, which are active complement inhibitors, are then provided by treatment of the above intermediate amine compounds with phosgene in aqueous media made alkaline with alkali metal carbonate or pyridine, neutralization, and precipitation from aqueous solution with alcohol.

This invention is concerned with a method of inhibiting the complement system in a body fluid, such as blood serum, which comprises subjecting body fluid complement to the action of an effective complement inhibiting amount of a compound encompassed within the formulae hereinabove. The method of use aspect of this invention is also concerned with a method of inhibiting the complement system in a warm-blooded animal which comprises administering to said animal an effective complement inhibiting amount of a compound encompassed within the formulae hereinabove. Body fluid can include blood, plasma, serum, synovial fluid, cerebrospinal fluid, or pathological accumulations of fluid such as pleural effusion, etc.

Compounds of the present invention find utility as complement inhibitors in body fluids and as such may be used to ameliorate or prevent those pathological reactions requiring the function of complement and in the therapeutic treatment of warm-blooded aniamls having immunologic diseases such as rheumatoid arthritis, systemic lupus erythematosus, certain kinds of glomerulonephritis, certain kinds of auto-allergic hemolytic anemia, certain kinds of platelet disorders and certain kinds of vascuculitis. The compounds herein may also be used in the therapeutic treatment of warm-blooded animals having non-immunologic diseases such as paroxysmal nocturnal hemoglobinuria, hereditary angioneurotic edema (treated with Suramin, etc.) and inflammatory states induced by the action of bacterial or lysosomal enzymes on the appropriate compelement components as for example, inflammation following coronary occlusion. They may also be useful in the treatment of transplant rejection and as blood culture or transport mediums.

The compounds of the present invention may be administered internally, e.g., orally or parenterally, e.g., intra-articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg,kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

While in general the sodium salts of the acids of the invention are suitable for parenteral use, other salts may also be prepared, such as those of primary amines, e.g., ethylamine; secondary amines, e.g., diethylamine or diethanol amine; tertiary amines, e.g., pyridine or triethylamine or 2-dimethylaminomethyldibenzofuran; aliphatic diamines, e.g., decamethylenediamine; and aromatic diamines, can be prepared. Some of these are soluble in water, others are soluble in saline solution, and still others are insoluble and can be used for purposes of preparing suspensions for injection. Furthermore, as well as the sodium salt, those of the alkali metals, such as potassium and lithium; of ammonia; and of the alkaline earth metals, such as calcium or magnesium, may be employed. It will be apparent, therefore, that these salts embrace, in general, derivatives of salt-forming cations.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid form in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injectio use.

The term dosage form, as described herein, refers to physically discrete units suitable as unitary dosage for warm-blooded animal subjects, each unit containing a predetermined quantity of active component calculated to produce the desired therapeutic effect in assocation with the required pharmaceutical diluent, carrier or vehicle. The specification for the novel dosage forms of this invention are indicated by characteristics of the active component and the particular therapeutic efect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or more of the following identified tests: (1) Test Code 026 (C1 inhibitor)—This test measures the ability of activated human C1 to destroy fluid phase human C2 in the presence of C4 and appropriate dilutions of the test compound. An active inhibitor protects C2 from C1 and C4; (ii) Test Code 035 (C3-C9 inhibitor)—This test determines the ability of the late components of human complement (C3-C9) to lyse EAC 142 in the presence of appropriate dilutions of the test compound. An active inhibitor protects EAC 142 from lysis by human C3-C9; (iii) Test Code 036 (C-Shunt inhibitor)—In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test—Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test—Lethal shock is produced in guinea pigs by an i.v. injection of anti-Forssman antiserum and the harmonic mean death time of treated guinea pigs is compared with that of simultaneous controls; (vi) Complement Level Reduction Test—In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test—Here, appropriate amounts of the test compound are added to a pool of guinea pig serum in vitro, after which the undiluted serum capillary tube assay referred to above is run. The concentration of compound inhibiting 50% is reported.

With reference to Table I, guinea pigs weighing about 300 g were dosed intravenously (i.v.) or intraperitoneally (i.p.) with 200 mg/kg of the test compound dissolved in saline and adjusted to pH 7–8. One hour after dosing, the guinea pigs were decapitated, blood was collected and the serum separated. The serum was tested for whole complement using the capillary tube assay. Percent inhibition was calculated by comparison with simultaneous controls. The results appear in Table I together with results of tests code 026, 035, 036, Cap 50, % inhibition and Forssman shock. Table I shows that the compounds of the invention possess highly significant in vitro and in vivo complement inhibiting activity in warm-blooded animals. Results obtained are listed in Table I.

Table II shows the complement inhibiting activity of the intermediate compounds of the invention.

TABLE I

| | Biological Activities | | | | In Vivo Activity (Guinea Pig) % Inhibition | | | | | |
|---|---|---|---|---|---|---|---|---|---|---|
| | Cl 026* | C-Late 035* | Shunt Inhibition 036* | | Intraperitoneal Time(Minutes) | | | Intravenous Time(Minutes) | | |
| Compound | Wells | Wells | Wells | Cap 50* | 30 | 60 | 120 | 2 | 30 | 120 |
| Suramin | +4** | +2** | — | 361 | −9 | −17 | −44 | | | |
| 5,5″-Ureylenebis[2′-methyl-5′-[(4,6,8-trisulfo-1-naphthyl)carbamoyl]isophthalanilic acid], octasodium salt | +5 | +2 | +2** | 249 | −17 | −50 | −57 | | | |
| 5,5″-Ureylenebis[2′-methyl-5′-[(4,6,8-trisulfo-1-naphthyl)carbamoyl]isophthalanilic acid], hexasodium salt | +5 | +2 | +2 | 295 | | | | | | |
| 8,8′-[Ureylenebis[[(2-sulfo-4,1-phenylenecarbonyl)imino](2-methyl-4,1-phenylene)sulfonyl]imino]]di-1,3,6-naphthalenetrisulfonic acid, octasodium salt | +4 | +2 | | 380 | | | | | | |
| 5,5′-Ureylenebis[(4-methyl-3,1-phenylenecarbonyl)imino]bis[N-(4,6,8-trisulfo-1-naphthyl)isophthalamic acid], hexasodium salt | +5 | +2 | +1 | 47 | | | | | | |
| 5,5′[Ureylenebis[(4-methyl-3,1-phenylene)carbonyl)imino]]bis[N-(4,6,8-trisulfo-1-naphthyl)isophthalamic acid, octasodium salt | +5 | — | — | | | | | | | |
| 8,8′-[Ureylenebis[[(2-sulfo-4,1-phenylenecarbonyl)imino]-(4-methyl-3,1-phenylenecarbonyl)imino]]di-1,3,5-naphthalenetrisulfonic acid, octasodium salt | +3 | +1 | +2 | 187 | | | | | | |
| 8,8′[Ureylenebis[[(2-sulfo-4,1-phenylenecarbonyl)imino][(4,6-dimethyl-3,1-phenylenesulfonyl)imino]]1,3,6-naphthalenetrisulfonic acid, octasodium salt | +5 | +2 | — | >330 | | | | | | |
| 8,8′-[Ureylenebis[[[(2-sulfo-1,4-phenylenecarbonyl)imino-1,4-phenylene]sulfonyl]imino]]di-1,3,6-naphthalenetrisulfonic acid, octasodium salt | +5 | N | +1 | 250 | | | | −92 | −56 | −25 |

*Code designation for tests employed as referred herein.
**Activity in wells a serial dilution assay. Higher well number indicates higher activity. The serial dilutions are two-fold.

TABLE II

| (INTERMEDIATES) Biological Activities | | | | |
|---|---|---|---|---|
| Compound | Cl 026* Wells | C-Late 035* Wells | Shunt Inhibition 036* Wells | Cap 50* |
| 5-Amino-2′-methyl-5′-[(4,6,8-trisulfo-1-naphthyl)carbamoyl]isophthalani- | +2** | N | N | |

TABLE II-continued

| | (INTERMEDIATES) Biological Activities | | | |
|---|---|---|---|---|
| Compound | Cl 026* Wells | C-Late 035* Wells | Shunt Inhibition 036* Wells | Cap 50* |
| lic acid, trisodium salt | | | | |
| 8-[5-(4-Amino-2-sulfobenzamido)-o-toluenesulfonamido]-1,3,6-naphthalenetrisulfonic acid, tetrasodium salt | +4 | N | N | >500 |
| 5-(3-Amino-p-toluamido)-N-(4,6,8-trisulfo-1-naphthyl)isophthalamic acid, trisodium salt | +3 | N | N | >500 |
| 8-[3-(4-Amino-2-sulfobenzamido)-p-toluamido]-1,3,5-naphthalenetrisulfonic acid, tetrasodium salt | +2 | N | N | |
| 5-Amino-2'-methyl-5'-(4,6,8-trisulfo-1-naphthylsulfamoyl)isophthalanilic acid, trisodium salt | +2 | N | N | |
| 8-[$N^3$-(4-Amino-2-sulfobenzoyl)-metanilamido]-1,3,6-naphthalenetrisulfonic acid, tetrasodium salt | +3 | N | N | |

*Code designation for tests employed as referred herein.
**Activity in wells a serial dilution assay. Higher well number indicates higher activity. The serial dilutions are two-fold.
N = Negative (no activity).

DETAILED DESCRIPTION OF THE INVENTION

Example 1

8-[5-(4-Amino-2-sulfobenzamido)-o-toluenesulfonamido]-1,3,6-naphthalenetrisulfonic acid, tetrasodium salt To a boiling solution of 100 g of 5-nitro-o-toluenesulfonic acid in 110 ml of water is added a solution of 53.6 g of sodium chloride in 150 ml of boiling water. The reaction mixture solidifies and is heated to boiling with the addition of sufficient water to provide solution. Then some of the water is boiled off and the mixture is allowed to stand for 16 hours. The solid formed is collected and dried to yield 92.5 g of 5-nitro-o-toluenesulfonic acid sodium salt.

A mixture of 50.0 g of the above compound, 125 ml of thionyl chloride and 1.3 ml of dimethylformamide is stirred and refluxed for 3 hours. The excess thionyl chloride is distilled off and the residue is reevapoted twice with ether. The residue is extracted with ether and methylene chloride. The extracts are evaporated and the residue is dissolved in ether and is filtered. The filtrate is concentrated while adding petroleum ether, then is placed in an icebox for 16 hours. The solid formed is collected and dried to yield 33.4 g of 5-nitro-o-toluenesulfonyl chloride.

A mixture of 17.0 g of 8-amino-1,3,6-naphthalenetrisulfonic acid, trisodium salt, 17.5 g of the preceding compound and 7.8 g of anhydrous sodium carbonate in 210 ml of water is stirred at room temperature for 18 hours, then an additional 0.5 g of sodium carbonate and 1.0 g of 5-nitro-o-toluenesulfonyl chloride is added and stirring is continued for 18 hours longer. The reaction mixture is evaporated and 100 ml of water is added with stirring. The mixture is filtered and 900 ml of absolute ethanol is added to the filtrate with stirring. The mixture is stirred for 2 hours, then the precipitate is collected and is washed with ethanol and ether and is dried to yield 20.8 g of 8-(5-nitro-o-toluenesulfonamido)-1,3,6-naphthalenetrisulfonic acid, trisodium salt.

A mixture of 20.0 g of the above product, 90.0 ml of water and 2.0 g of 10% palladium-on-carbon catalyst is hydrogenated as described in Example 1. The reaction mixture is filtered through diatomaceous earth and the filtrate is evaporated. The residue is dissolved in a minimum amount of water, then is added dropwise to 800 ml of stirred absolute ethanol. The mixture is stirred for 2 hours and is allowed to stand for 48 hours. A light yellow solid is collected, washed with ethanol and ether, then is dried to yield 15.0 g of 8-(5-amino-o-toluenesulfonamido)-1,3,6-naphthalenetrisulfonic acid, trisodium salt.

A solution of 100 g of 5-nitro-o-toluenesulfonic acid in 600 ml of water plus 80 ml of 5 N sodium hydroxide is heated to 90° C. in a 2 liter Erlenmeyer flask, then 240 g of potassium permanganate is added portionwise to maintain reflux over one hour and 15 minutes. The mixture is filtered and the residue is washed with water. The combined filtrate and washings are concentrated in vacuo and allowed to crystallize to give 86.2 g of crude 4-nitro-2-sulfobenzoic acid, sodium potassium salt. Recrystallization from water gives 71.3 g of purified product.

The total product above is dissolved in 250 ml of water plus 35 ml of concentrated hydrochloric acid by warming on a steam bath. The solution is then diluted with 300 ml of ethyl alcohol and allowed to crystallize at room temperature. The mixture is allowed to stand 48 hours in a chill room, then is filtered. The precipitate is washed with cold 50% aqueous ethanol, then with ethanol and ether. The material is recrystallized from 200 ml of water and is dried at 110° C. to give 52.0 g of 4-nitro-2-sulfobenzoic acid-2-sodium salt.

A 50.0 g portion of the preceding compound and 500 g of thionyl chloride is stirred and refluxed for 19 hours. The mixture is evaporated in vacuo and the residue is warmed with 300 ml of toluene and is filtered. The filtrate is concentrated in vacuo and the product is crystallized twice from toluene to give 30.4 g of 4-nitro-2-sulfobenzoic acid anhydride.

To a stirred solution of 9.0 g of 8-(5-amino-o-toluenesulfonamido)-1,3,6-naphthalenetrisulfonic acid, trisodium salt, and 3.34 g of sodium acetate trihydrate in 47.0 ml of water chilled to 0° C. in an ice bath is added 4.29 g of 4-nitro-2-sulfobenzoic acid anhydride in one portion. The mixture is stirred for a total of 10 minutes in the ice bath and the undissolved material is separated. The solution, at 0° C., is acidified with 1.38 ml of concentrated hydrochloric acid, then is added dropwise, with vigorous stirring, to 750 ml of absolute ethanol. The product is collected, washed with 85% aqueous ethanol, ethanol and ether and is dried to yield 11.75 g of 8-[5-(4-nitro-2-sulfobenzamido)-o-toluenesulfonamido]-1,3,6-naphthalenetrisulfonic acid, tetrasodium salt.

A mixture of 9.7 g of the preceding product, 80.0 ml of water and 1.0 g of 10% palladium-on-carbon catalyst is hydrogenated as previously described. The mixture is filtered and the filtrate is evaporated, dissolved in water and added dropwise to 650 ml of ethanol. The resulting mixture is stirred for 2 hours, then the product is separated and washed with ethanol and ether and dried to give 8.1 g of the product of the Example.

Example 2

8-[5-(4-Amino-2-sulfobenzamido)-o-toluenesulfonamido]-1,3,5-naphthalenetrisudfonic acid, tetrasodium salt Following the procedure of Example 1, employing 8-amino-1,3,5-naphthalenetrisulfonic acid, trisodium salt provides the product of the Example.

EXAMPLE 3

8,8'-[Ureylenebis[(2-sulfo-4,1-phenylenecarbonyl)imino(6-methyl-3,1-phenylenesulfonyl)imino]]di-1,3,6-naphthalenetrisulfonic acid, octasodium salt A cooled solution of 4.0 g of the product of Example 1, and 2.49 ml of pyridine in 35.0 ml of water is phosgenated until acidic to Congo Red indicator paper. An additional 1.38 ml of pyridine is added and phosgene is bubbled in again until acidic to Congo Red indicator. The solution is neutralized with pyridine and poured into 650 ml of absolute ethanol with stirring. The mixture is stirred for 30 minutes, then the solid is separated, washed with ethanol and ether and dried. The material is dissolved in 30.0 ml of water. The solution is adjusted to pH 8.0 with 5 N sodium hydroxide, then is neutralized with glacial acetic acid and poured into 800 ml of absolute ethanol with stirring. The mixture is stirred for 30 minutes and is evaporated. The residue is dissolved in 25.0 ml of water and is added to 500 ml of absolute ethanol with stirring. An additional 300 ml of ethanol is added and the mixture is stirred for 16 hours, then is evaporated. The residue is dissolved in 35.0 ml of water, the solution is adjusted to pH 7.0 and is slowly added to 500 ml of absolute ethanol with stirring. The solution is concentrated to 400 ml on a steam bath while adding water to provide a gum and a fluffy solid. The fluffy material is separated, washed with ethanol and ether and dried to yield 2.0 g of the product of the Example.

Example 4

8,8'-[Ureylenebis[(2-sulfo-4,1-phenylenecarbonyl)imino(6-methyl-3,1-phenylenesulfonyl)imino]]di-1,3,5-naphthalenetrisulfonic acid, octasodium salt Following the procedure of Example 3, phosgenation of the product of Example 2 provides the product of the Example.

EXAMPLE 5

8-[5-(4-Amino-2-sulfobenzamido)-2,4-xylenesulfonamido]-1,3,6-naphthalenetrisulfonic acid, tetrasodium salt A 42.3 g amount of 2,4-dimethyl-5-nitrobenzenesulfonic acid in 50 ml of water is heated to 70° C., then a solution of 25.0 g of sodium chloride in 70.0 ml of water is added forming a solid. Water is added to a total volume of 300 ml and the mixture is heated to boiling. The solution is filtered and the filter is washed with 100 ml of hot water which is added to the filtrate. The filtrate is concentrated to 300 ml and is allowed to cool. The solution is placed in an icebox for 16 hours with formation of a crystalline precipitate. The crystals are collected by filtration to yield 34.6 g of product. The filtrate is concentrated to 150 ml and is cooled and filtered to provide an additional 4.2 g of product. The fractions are combined to provide 38.8 g of 5-nitro-2,4-xylenesulfonic acid, sodium salt.

A mixture of the entire product above, 100 ml of thionyl chloride and 1.0 ml of dimethylformamide (dried over molecular sieves) is heated at reflux for 3 hours. The mixture is allowed to cool at room temperature, then is evaporated in vacuo. Ether is added and the mixture is re-evaporated. The residue is extracted several times with boiling ether. The ether extracts are concentrated to 300 ml and allowed to cool. The crystals formed arecollected by filtration to provide 2.0 g of product. The filtrate is evaporated and the residue is extracted once with boiling methylene chloride. The extract is evaporated and the residue is dissolved in ether, concentrated to a small volume and cooled. The crystalline precipitate is collected to yield 22.0 g of additional product. The fractions are combined to provide 24.0 g of 5-nitro-2,4-xylenesulfonyl chloride.

A mixture of 11.0 g of 8-amino-1,3,6-naphthalenetrisulfonic acid, trisodium salt, 14.0 g of the preceding product, 6.15 g of anhydrous sodium carbonate and 140 ml of water is stirred with heat until thin layer chromatography shows the reaction is complete. The mixture is filtered and the filtrate is concentrated in vacuo removing and discarding crops of solid as they precipitate. The final filtrate is evaporated, the residue is dissolved in water, absolute ethanol is added and the mixture is stirred for one hour and filtered. The solid is washed with ethanol and ether giving 9.8 g of 8-(5-nitro-2,4-xylenesulfonamido)-1,3,6-naphthalenetrisulfonic acid, trisodium salt. An additional 1.28 g of the same product is derived from second and third crops of the filtrate.

A mixture of 11.0 g of the above product, 50.0 ml of water and 1.0 g of 10% palladium-on-carbon catalyst is hydrogenated as described in Example 1. The reaction mixture is filtered through diatomaceous earth and the filter is washed with water. The filtrate is evaporated, the residue is dissolved in 30 ml of water and is added to 450 ml of absolute ethanol. The mixture is stirred for ½ hour and the product is separated by filtration. An additional crop of product is derived from reprecipitation of the filtrate. The combined product is washed with ether and dried to yield 7.52 g of 8-(5-amino-2,4-xylenesulfonamido)-1,3,6-naphthalenetrisulfonic acid, trisodium salt.

To a stirred solution of 5.0 g of the product above and 1.81 g of sodium acetate trihydrate in 26.0 ml of water chilled to 0° C. in an ice bath is added 2.29 g of 4-nitro-2-sulfobenzoic acid anhydride in one portion. The mixture is stirred for a total of 10 minutes in the ice bath and the undissolved material is separated. The solution at 0° C. is acidified with 0.74 ml of concentrated hydrochloric acid and 200 ml of absolute ethanol is added to precipitate a solid. The product is separated by filtration, washed with ethanol and ether and dried. The filtrate is evaporated and the resulting residue is dissolved in a minimum amount of water, then absolute ethanol is added to precipitate additional product. The product fractions are combined to provide 5.84 g of 8-[5-(4-nitro-2-sulfobenzamido)-2,4-xylenesulfonamido]-1,3,6-naphthalenetrisulfonic acid, tetrasodium salt.

A mixture of 5.0 g of the preceding product, 50.0 ml of water and 700 mg of 10% palladium-on-carbon catalyt is hydrogenated as previously described. The reaction mixture is filtered through diatomaceous earth and the filtrate is evaporated. The residue is dissolved in a minimum amount of water and is added slowly to 250 ml of absolute ethanol with stirring. The precipitate is collected, washed with ethanol and ether and dried to yield 4.05 g of the product of the Example.

Example 6

8-[5-(4-Amino-2-sulfobenzamido)-2,4-xylenesulfonamido]-1,3,5-naphthalenetrisulfonic acid, tetrasodium salt Following the procedure of Example 5, employing 8-amino-1,3,5-naphthalenetrisulfonic acid, trisodium salt provides the product of the Example.

Example 7

8,8'-[Ureylenebis[(2-sulfo-4,1-phenylenecarbonyl)imino(4,6-dimethyl-3,1-phenylenesulfonyl)imino]]di-1,3,6-naphthalenetrisulfonic acid, octasodium salt A cooled solution of 4.0 g of the product of Example 5 and 2.35 ml of pyridine in 35.0 ml of water is phosgenated until acidic to Congo Red indicator paper. An additional 1.1 ml of pyridine is added and phosgene is bubbled in again until acidic to Congo Red indicator. The solution is neutralized with pyridine and poured into 650 ml of absolute ethanol with stirring. The mixture is stirred for 30 minutes, then the solid is separated, washed with ethanol and ether and dried. The crude product is dissolved in 30.0 ml of water and is adjusted to pH 8.0 with 5 N sodium hydroxide. The solution is neutralized to pH 7.0 with glacial acetic acid and is poured into 650 ml of absolute ethanol. The mixture is stirred for one hour, then is evaporated. The residue is dissolved in 30.0 ml of water, several drops of glacial acetic acid are added and the solution is added to 800 ml of absolute ethanol with stirring. The mixture is concentrated to 400 ml on a steam bath while adding water, with separation of an oil. The aqueous solution is decanted from the oil and ethanol is added to it to provide a fine precipitate. The precipitate is separated, washed with ethanol and ether and dried to yield 2.15 g of the product of the Example.

Example 8

8,8'-[Ureylenebis[(2-sulfo-4,1-phenylenecarbonyl)imino(4,6-dimethyl-3,1-phenylenesulfonyl)imino]]di-1,3,5-naphthalenetrisulfonic acid, octasodium salt Following the procedure of Example 7, phosgenation of the product of Example 6 provides the product of the Example.

EXAMPLE 9

5-Amino-2'-methyl-5'-(4,6,8-trisulfo-1-naphthylsulfamoyl)-isophthalanilic acid, trisodium salt A mixture of 25.0 g of p-toluenesulfonic acid and 95.0 ml of concentrated nitric acid is heated on a steam bath for 30 minutes. The solution is poured into 250 ml of water and is evaporated at reduced pressure. A small quantity of water is added and the mixture is evaporated again. This step is repeated two additional times to remove all of the nitric acid. The mixture is neutralized with a saturated solution of sodium carbonate and is evaporated affording a yellow solid. The solid is slurried with absolute ethanol, is collected by filtration and is washed twice with both ethanol and ether to give 10.3 g of product. The filtrate is allowed to stand and the solid formed is collected and washed as above to provide 10.0 g of additional product and a total of 20.3 g of 3-nitro-p-toluenesulfonic acid, sodium salt.

A mixture of 20.0 g of the above compound, 250 ml of thionyl chloride and 20.0 ml of dimethylformamide is refluxed for 16 hours. The excess thionyl chloride is removed by distillation, then the mixture is cooled and ether is added. The mixture is evaporated and the crude product is distilled under vacuum. The fraction recovered at a pressure of 1.0–1.5 mm of mercury and a boiling point of 152°–154° C. provides 11.5 g of 3-nitro-p-toluenesulfonyl chloride.

An 8.0 g portion of the preceding product is added to a stirred solution of 7.2 g of 8-amino-1,3,5-naphthalenetrisulfonic acid, trisodium salt and 1.7 g of anhydrous sodium carbonate in 30.0 ml of water with separation of an oil. The mixture is stirred for 16 hours and then is evaporated. The residue is dissolved in water and absolute ethanol is added to provide a precipitate. The product is collected and washed with ethanol and ether. The filtrate is evaporated and the residue is precipitated as above to provide additional product. A third crop is obtained from the final filtrate to provide a total of 8.6 g of 8-(3-nitro-p-toluenesulfonamido)-1,3,5-naphthalenetrisulfonic acid, trisodium salt.

A mixture of 8.0 g of the above product, 160 ml of water and 800 mg of 10% palladium-on-carbon catalyst is hydrogenated on a Parr shaker until no additional hydrogen is absorbed. The resulting mixture is filtered through diatomaceous earth and the filtrate is evaporated. The residue is dissolved in hot water and is filtered. The filtrate is triturated with ethanol until cloudiness persists, then is allowed to stand at room temperature for 16 hours. The mixture is filtered and the filtrate is evaporated to afford a gummy material which is dissolved in a small amount of water and triturated with ethanol. An additional 200 ml of ethanol is added and the mixture is stirred for one hour to provide a solid. The solid is collected and washed with ethanol and ether to yield 4.6 g of 8-(3-amino-p-toluenesulfonamido)-1,3,5-naphthalenetrisulfonic acid, trisodium salt.

To a stirred solution of 2.5 g of the above product, 20 ml of water and 428 mg of anhydrous sodium carbonate is added 1.2 g of 3-carbomethoxy-5-nitrobenzoyl chloride (prepared as described below). The mixture is stirred at room temperature for 16 hours, then is evaporated. The residue is dissolved in hot water and is filtered. The filtrate is triturated with absolute ethanol and is allowed to cool forming a gelatinous mass. The material is collected and washed with ethanol and ether to yield 2.5 g of 2'-methyl-5-nitro-5'-(4,6,8-trisulfo-1-naphthylsulfamoyl)isophthalanilic acid, methyl ester, trisodium salt as a light tan powder.

To a stirred solution of 2.25 g of the above product in 20 ml of water is added 3.0 ml of 1 N sodium hydroxide. The mixture is stirred at room temperature for 16 hours, then is acidified with glacial acetic acid and is evaporated. The resulting solid is dissolved in hot water, then is triturated with ethanol until crystallization occurs. The mixture is cooled, the precipitate is collected and washed with ethanol and ether. The product is reprecipitated from water with ethanol, then is collected and is washed as above and dried to yield 1.52 g of 2'-methyl-5-nitro-5'-[(4,6,8-trisulfo-1-naphthyl)sulfamoyl]isophthalanilic acid, trisodium salt.

A mixture of 1.25 g of the preceding product, 110 ml of water and 140 mg of 10% palladium-on-carbon catalyst is hydrogenated in a Parr shaker until no additional hydrogen is absorbed. The resulting mixture is filtered, and the filtrate is evaporated. The residue is dissolved in hot water and ethanol is added. The mixture is filtered and the filtrate is evaporated yielding a yellow-white powder. The powder is washed with ether and dried to provide 950 mg of the product of the Example.

Preparation of 3-carbomethoxy-5-nitrobenzoyl chloride

A mixture of 7.46 g of potassium hydroxide in 87.5 ml of methanol is added to a stirred solution of 3.175 g of the preceding product in 331.0 ml of acetone. A solid is precipitated and stirring is continued for 16 hours. The solid (A) is filtered off, washed with ether and set aside. The filtrate is evaporated, the residue is extracted with 125 ml of warm water and is filtered. The filtrate is acidified with dilute hydrochloric acid to produce a precipitate which is collected and dried to yield 3.4 g of product. The solid (A) is extracted with 250 ml of warm water and is filtered. The filtrate is filtered again at room temperature, acidified with dilute hydrochloric acid and cooled. The precipitate is collected and dried to give 18.25 g of additional product identified as 5-nitro-isophthalic acid, 3-methyl ester.

A mixture of 18.38 g of the above product, 60 ml of thionyl chloride and 0.37 ml of dimethylformamide is heated at 60° C. for 2.5 hours. The solution is evaporated, then is treated with toluene, and again is evaporated. The residue is slurried in hot diethyl ether and the ether volume is reduced by evaporation. The mixture is chilled and filtered. The precipitate is washed with cold ether and is dried. The material is extracted with 500 ml of boiling hexane by decantation. The hexane is cooled and filtered to yield 14.1 g of 3-carbomethoxy-5-nitrobenzoyl chloride.

EXAMPLE 10

5-Amino-2'-methyl-5'-(3,6,8-trisulfo-1-naphthylsulfamoyl)-isophthalanilic acid, trisodium salt Following the procedure of Example 9, employing 8-amino-1,3,6-naphthalenetrisulfonic acid, trisodium salt yields the product of the Example.

EXAMPLE 11

5,5''-Ureyelenbis[2'-methyl-5'-(4,6,8-trisulfo-1-naphthylsulfamoyl)isophthalanilic acid], octasodium salt A solution of 750 mg of the product of Example 9, 10 ml of water and 102 mg of anhydrous sodium carbonate is phosgenated until acidic to Congo Red indicator paper. The solution is neutralized with sodium carbonate, then phosgenated again until acidic. The solution is neutralized as above and then acidified with glacial acetic acid. The reaction mixture is evaporated and the residue is dissolved in water. Ethanol is added providing an oil. The aqueous solution is decanted and ethanol is added again to separate additional oil. The solution is decanted again, ethanol is added and the resulting precipitate is filtered, washed with ethanol and ether and dried affording 400 mg of the product of the Example.

EXAMPLE 12

5,5''-Ureylenebis[2'-methyl-5'-(3,6,8-trisulfo-1-naphthylsulfamoyl)isophthalanilic acid], octasodium salt.

Following the procedure of Example 11, phosgenation of the product of Example 10 provides the product of the Example.

EXAMPLE 13

8-[$N^3$-(4-Amino-2-sulfobenzoyl)metanilamido]-1,3,6-naphthalenetrisulfonic acid, tetrasodium salt To a stirred solution of 21.9 g of 8-amino-1,3,6-naphthalenetrisulfonic acid, trisodium salt and 11.4 g of anhydrous sodium carbonate in 280 ml of water is added 24.0 g of m-nitrobenzenesulfonyl chloride. The mixture is stirred at room temperature for 16 hours, then an additional 1.0 g of sodium carbonate and 2.0 g of m-nitrobenzenesulfonyl chloride are added and stirring is continued for 3 hours longer. The mixture is evaporated and the residue is dissolved in 200 ml of water. A copious amount of absolute ethanol is added and the solid formed is collected and washed with ethanol and ether, then is dried to yield 26.1 g of 8-m-nitrobenzenesulfonamido-1,3,6-naphthalenetrisulfonic acid, trisodium salt.

A mixture of 26.1 g of the preceding product, 175 ml of water and 2.09 g of palladium-on-carbon catalyst is hydrogenated in a Parr shaker until no additional hydrogen is absorbed. The resulting mixture is filtered through diatomaceous earth and the filtrate is evaporated. The residue is dissolved in 60.0 ml of water and, with stirring, 400 ml of absolute ethanol is added, to precipitate a solid. The mixture is allowed to stir for 2 hours, then is filtered. The product is washed with absolute ethanol and ether to give 25.3 g of 8-metanilamido-1,3,6-naphthalenetrisulfonic acid, trisodium salt.

To a stirred and chilled solution (ice-bath at 0° C.) of 9.0 g of the above product and 3.42 g of sodium acetate trihydrate in 48.0 ml of water is added, in one portion, 4.35 g of 4-nitro-2-sulfobenzoic acid anhydride. The mixture is stirred for a total of 10 minutes at 0° C. The undissolved material is removed by filtration and the filtrate in the ice-bath is acidified with 1.41 ml of concentrated hydrochloric acid, then 400 ml of absolute ethanol is added to separate the product. The material is collected by filtration and is washed with 85% aqueous ethanol, then ethanol and ether to yield 3.87 g of product. Additional product (5.3 g) is recovered by adding ethanol to the filtrate above, the filtering and washing as described. The total yield is 9.1 g of 8-[$N^3$-(4-nitro-2-sulfobenzoyl)metanilzmido]-1,3,6-naphthalenetrisulfonic acid, tetrasodium salt.

A mixture of 11.1 g of the preceding compound (prepared as described above), 90.0 ml of water and 1.0 g of 10% palladium-on-carbon catalyst is hydrogenated in a Parr shaker until no additional hydrogen is absorbed. The resulting mixture is filtered and the filtrate is evaporated to a glass. The glass is triturated in hot ethanol, then is collected by filtration and is washed with ethanol and ether and dried to yield 10.58 g of the product of the Example.

EXAMPLE 14

8,8'-[Ureylenebis[(2-sulfo-1,4-phenylenecarbonyl)imino(3,1-phenylenesulfonyl)imino]]di-1,3,6-naphthalenetrisulfonic acid, octasodium salt A solution of 5.0 g of the product of Example 13, and 3.0 ml of pyridine in 40 ml of water is phosgenated until it is acidic to Congo Red indicator paper. An additional 2.0 ml of pyridine is added and phosgene is bubbled in again until the solution is acidic. The solution is neutralized with pyridine and is added to 400 ml of absolute ethanol with stirring to provide a gum. The supernatant is decanted, and fresh ethanol is added to the gum. The mixture is stirred vigorously for 2 hours, then is filtered. The material on the filter is washed with ethanol and ether and is air dried, then is dissolved in 25.0 ml of water and basified to pH (8-9) with 5 N sodium hydroxide. The solution is neutralized with glacial acetic acid and filtered. The filtrate is added to 400 ml of absolute ethanol with stirring to precipitate a light pink solid. The solid is separated and is washed with ethanol and ether and is dried to yield 4.0 g of the product of the Example.

EXAMPLE 15

| Preparation of Compressed Tablet | |
|---|---|
| Ingredient | mg/Tablet |
| Active Compound | 0.5–500 |
| Dibasic Calcium Phosphage N.F. | qs |
| Starch USP | 40 |
| Modified Starch | 10 |
| Magnesium Stearate USP | 1–5 |

EXAMPLE 16

| Preparation of Compressed Tablet - sustained Action | |
|---|---|
| Ingredient | mg/Tablet |
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 17

| Preparation of Hard Shell Capsule | |
|---|---|
| Ingredient | mg/Capsule |
| Active Compound | 0.5–500 |
| Lactose, Spray Dried | qs |
| Magnesium Stearate | 1–10 |

EXAMPLE 18

| Preparation of Oral Liquid (Syrup) | |
|---|---|
| Ingredient | % W/V |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 19

| Preparation of Oral Liquid (Elixir) | |
|---|---|
| Ingredient | % W/V |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 20

| Preparation of Oral Suspension (Syrup) | |
|---|---|
| Ingredient | % W/V |
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 21

| Preparation of Injectable Solution | |
|---|---|
| Ingredient | % W/V |
| Active Compound | 0.05–5 |
| Benzyl Alcohol N.F. | 0.9 |
| Water for Injection | 100.0 |

EXAMPLE 22

| Preparation of Injectable Oil | |
|---|---|
| Ingredient | % W/V |
| Active Compound | 0.05–5 |
| Benzyl Alcohol | 1.5 |
| Sesame Oil qs ad | 100.0 |

EXAMPLE 23

| Preparation of Intra-Articular Product | |
|---|---|
| Ingredient | Amount |
| Active Compound | 2–20 mg |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs ad | 100% |

EXAMPLE 24

| Preparation of Injectable Depo Suspension | |
|---|---|
| Ingredient | % W/W |
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol N. F. | 0.9 |
| HCl to pH 6–8 | qs |
| Water for Injection qs ad | 100.0 |

EXAMPLE 25

| Preparation of Dental Paste | |
|---|---|
| Ingredient | % W/W |
| Active Compound | 0.05–5 |
| Zinc Oxide | 15 |
| Polyethylene Glycol 4000 USP | 50 |
| Distilled Water qs | 100 |

EXAMPLE 26

| Preparation of Dental Ointment | |
|---|---|
| Ingredient | % W/W |
| Active Compound | 0.05–5 |
| Petrolatum, White USP qs | v 100 |

EXAMPLE 27

| Preparation of Dental Cream | |
|---|---|
| Ingredient | % W/W |
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methylparaben USP | 0.18 |
| Propyl Paraben USP | 0.02 |
| Distilled Water qs | 100 |

EXAMPLE 28

| Preparation of Topical Cream | |
|---|---|
| Ingredient | % W/W |
| Active Compound | 0.05–5 |
| Sodium Laurylsulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 29

| Preparation of Topical Ointment | |
|---|---|
| Ingredient | % W/W |
| Active Compound | 0.05–5 |
| Cholesterol | 3 |
| Stearyl Alcohol | 3 |

| -continued | |
|---|---|
| Preparation of Topical Ointment | |
| Ingredient | % W/W |
| White Wax | 8 |
| Petrolatum, White USP qs | 100 |

EXAMPLE 30

| Preparation of Spray Lotion (non-Aerosol) | |
|---|---|
| Ingredient | % W/W |
| Active Compound | 0.05–5 |
| Isopropyl Myristate | 20 |
| Alcohol (Denatured) qs | 100 |

EXAMPLE 31

| Preparation of Buccal Tablet | |
|---|---|
| Ingredient | g/Tablet |
| Active Ingredient | 0.00325 |
| 6 × Sugar | 0.29060 |
| Acacia | 0.01453 |
| Soluble Starch | 0.01453 |
| F.D. & C. Yellow No. 6 Dye | 0.00049 |
| Magnesium Stearate | 0.00160 |
| | 0.32500 |

The final tablet will weigh about 325 mg. and may be compressed into buccal tablets in flat faced or any other tooling shape convenient for buccal administration.

EXAMPLE 32

| Preparation of Lozenge | |
|---|---|
| Ingredient | g/Lozenge |
| Active Ingredient | 0.0140 |
| Kompact ® Sugar (Sucrest Co.) | 0.7138 |
| 6 × Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝" flat based lozenge tooling. Other shapes may also be utilized.

We claim:

1. A compound of the formulae:

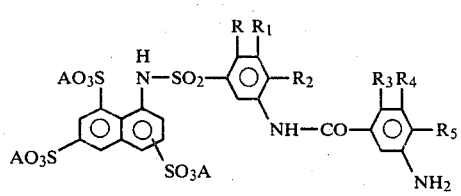

and

-continued

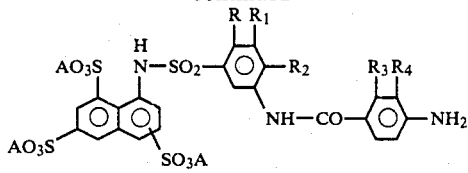

wherein R and $R_2$ are selected from the group consisting of hydrogen and methyl; $R_1$ and $R_4$ are selected from the group consisting of hydrogen and —COOB, wherein B is selected from the group consisting of hydrogen and a pharmaceutically acceptable salt cation; $R_3$ is selected from the group consisting of hydrogen and —$SO_3A$, wherein A is a pharmaceutically acceptable salt cation; $R_5$ is selected from the group consisting of hydrogen and methyl; with the proviso that $R_1$, $R_3$ and $R_4$ may not all be hydrogen; with the second proviso that $R_2$ and $R_5$ may not both be hydrogen; with the third proviso that neither phenyl moiety can contain both —$SO_3A$ and —COOB.

2. The compound according to claim 1, 8-[5-(4-Amino-2-sulfobenzamido)-o-toluenesulfonamido]-1,3,6-naphthalenetrisulfonic acid, tetrasodium salt.

3. The compound according to claim 1, 8-[5-(4-Amino-2-sulfobenzamido)-o-toluenesulfonamido]-1,3,5-naphthalenetrisulfonic acid, tetrasodium salt.

4. The compound according to claim 1, 8-[5-(4-Amino-2-sulfobenzamido)-2,4-xylenesulfonamido]-1,3,6-naphthalenetrisulfonic acid, tetrasodium salt.

5. The compound according to claim 1, 8-[5-(4-Amino-2-sulfobenzamido)-2,4-xylenesulfonamido]-1,3,5-naphthalenetrisulfonic acid, tetrasodium salt.

6. The compound according to claim 1, 5-Amino-2'-methyl-5'-(4,6,8-trisulfo-1-naphthylsulfamoyl)-isophthalanilic acid, trisodium salt.

7. The compound according to claim 1, 5-Amino-2'-methyl-5'-(3,6,8-trisulfo-1-naphthylsulfamoyl)-isophthalanilic acid, trisodium salt.

8. The compound according to claim 1, 8-[$N^3$-(4-Amino-2-sulfobenzoyl)metanilamido]-1,3,6-naphthalenetrisulfonic acid, tetrasodium salt.

* * * * *